(12) United States Patent
Whittam et al.

(10) Patent No.: US 11,610,319 B2
(45) Date of Patent: Mar. 21, 2023

(54) SYSTEM AND METHOD FOR OBTAINING THERMAL IMAGE DATA OF A BODY PART AND THERMAL IMAGER

(71) Applicant: NPL MANAGEMENT LIMITED, Teddington (GB)

(72) Inventors: Aaron Whittam, Teddington (GB); Rob Simpson, Teddington (GB)

(73) Assignee: NPL MANAGEMENT LIMITED, Teddington (GB)

( * ) Notice: Subject to any disclaimer, the term of this patent is extended or adjusted under 35 U.S.C. 154(b) by 0 days.

(21) Appl. No.: 17/260,889

(22) PCT Filed: Jul. 16, 2019

(86) PCT No.: PCT/GB2019/051984
§ 371 (c)(1),
(2) Date: Jan. 15, 2021

(87) PCT Pub. No.: WO2020/016569
PCT Pub. Date: Jan. 23, 2020

(65) Prior Publication Data
US 2021/0264615 A1    Aug. 26, 2021

(30) Foreign Application Priority Data

Jul. 16, 2018  (GB) ..................................... 1811620

(51) Int. Cl.
*G06T 7/194*        (2017.01)
*G06T 7/174*        (2017.01)
(Continued)

(52) U.S. Cl.
CPC .............. *G06T 7/194* (2017.01); *A61B 5/004* (2013.01); *A61B 5/015* (2013.01); *A61B 5/445* (2013.01);
(Continued)

(58) Field of Classification Search
CPC ..... A61B 5/015; A61B 2576/02; A61B 5/004; A61B 5/0261; A61B 5/445; A61B 5/447;
(Continued)

(56) References Cited

U.S. PATENT DOCUMENTS 7,640,140 B2    12/2009 Ruchti et al.
2005/0240090 A1    10/2005 Ruchti et al.
(Continued)

FOREIGN PATENT DOCUMENTS

WO    2018/158504 A1    9/2018

OTHER PUBLICATIONS

Liu Chanjuan et al. : "Automatic detection of diabetic foot complications with infrared thermography by asymmetric analysis", Journal of Biomedical Optics, SPIE, vol. 20, No. 2, Feb. 1, 2015, pp. 1-10,.*

(Continued)

*Primary Examiner* — Dakshesh D Parikh
(74) *Attorney, Agent, or Firm* — Thomas Horstemeyer, LLP

(57) ABSTRACT

A computer-implemented method for obtaining thermal image data of a body part and a thermal imager are disclosed. The method comprises receiving image data of a body part, the image data including thermal image data, the thermal image data including thermal image data of the body part and background thermal image data, applying a classifier to the image data to detect a profile of the body part, the classifier being configured to use image data other than the thermal image data to perform the detection, generating a mask from said profile, and applying the mask to the thermal image data to remove the background thermal image data and obtain thermal image data of the body part.

13 Claims, 5 Drawing Sheets

(51) Int. Cl.
*G06T 7/70* (2017.01)
*H04N 13/239* (2018.01)
*A61B 5/00* (2006.01)
*A61B 5/01* (2006.01)
*G06K 9/62* (2022.01)
*G06T 7/00* (2017.01)
*H04N 5/247* (2006.01)
*H04N 5/262* (2006.01)
*G06V 40/10* (2022.01)

(52) U.S. Cl.
CPC .......... *A61B 5/7267* (2013.01); *G06K 9/6256* (2013.01); *G06K 9/6267* (2013.01); *G06T 7/0014* (2013.01); *G06T 7/174* (2017.01); *G06T 7/70* (2017.01); *G06V 40/10* (2022.01); *H04N 5/247* (2013.01); *H04N 5/2628* (2013.01); *H04N 13/239* (2018.05); *G06T 2207/10012* (2013.01); *G06T 2207/10048* (2013.01); *G06T 2207/20081* (2013.01); *G06T 2207/20084* (2013.01); *G06T 2207/30088* (2013.01); *G06T 2207/30196* (2013.01); *G06V 2201/03* (2022.01)

(58) Field of Classification Search
CPC ........ A61B 5/7267; G06T 2207/10012; G06T 2207/10048; G06T 2207/20081; G06T 2207/20084; G06T 2207/30088; G06T 7/0014; G06T 7/174; G06T 7/194; G06T 2207/10016; G06T 2207/10024; G06T 2207/30096; G06T 2207/30196; G06T 7/0016; G06T 7/11; G06T 7/70; G06T 2207/20172; G06K 2209/05; G06K 9/00362; G06K 9/6256; G06K 9/6267; G16H 30/40; H04N 13/239; H04N 5/247; H04N 5/2628

See application file for complete search history.

(56) References Cited

U.S. PATENT DOCUMENTS

| | | | |
|---|---|---|---|
| 2011/0215930 A1* | 9/2011 | Lee | G08B 23/00 382/128 |
| 2016/0183879 A1* | 6/2016 | Goldish | A61B 5/0077 600/407 |
| 2016/0206211 A1* | 7/2016 | Naimi | G06T 7/0012 |
| 2016/0231807 A1* | 8/2016 | Ogasawara | H04N 5/33 |
| 2020/0138360 A1* | 5/2020 | Fan | A61B 5/14551 |

OTHER PUBLICATIONS

Oliveira Gabriell et al.: "Deep learning for human part discovery in images", 2016 IEEE International Conference on Robotics and Automation (ICRA), IEEE, May 16, 2016, pp. 1634-1641.*

Sudha B. G. et al.: "Thermal image acquisition and segmentation of human foot", 2017 4th International Conference on Signal Processing and Integrated Networks (SPIN), IEEE, Feb. 2, 2017, pp. 80-85.*

Goyal et al., "DFUNet: Convolutional Neural Networks for Diabetic Foot Ulcer Classification", Nov. 28, 2017, XP055474122, Retrieved from the Internet: URL:https://arxiv.org/pdf/1711.10448.pdf [retrieved on May 9, 2018].

First Examiner Report for Indian Patent Application No. 202127006336 dated Oct. 17, 2022.

* cited by examiner

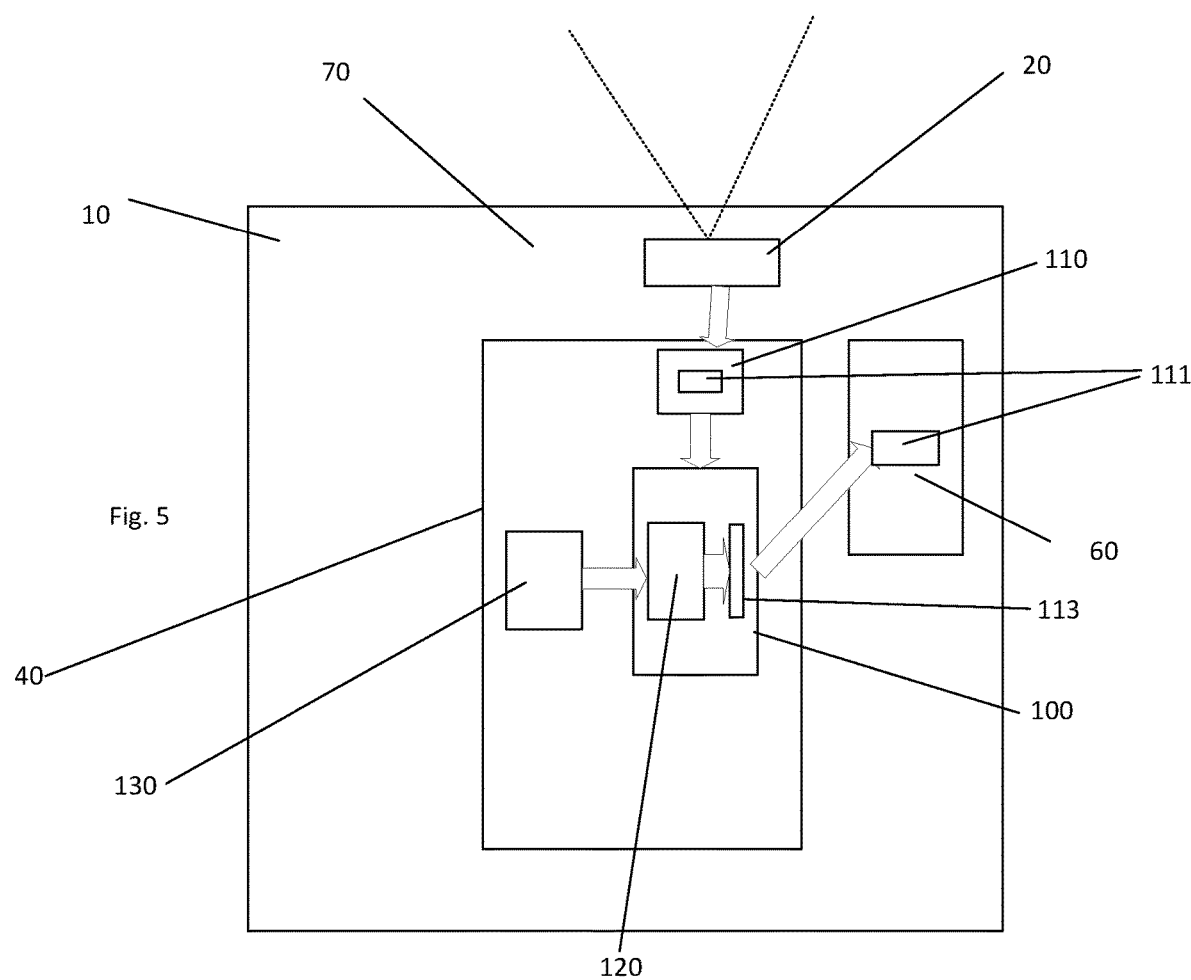

SYSTEM AND METHOD FOR OBTAINING THERMAL IMAGE DATA OF A BODY PART AND THERMAL IMAGER

CROSS-REFERENCE TO RELATED APPLICATIONS

This application is a 35 U.S.C. § 371 National Stage Patent Application of, and claims priority to, Patent Cooperation Treaty Application number PCT/GB2019/051984, filed on 16 Jul. 2019, and entitled "SYSTEM AND METHOD FOR OBTAINING THERMAL IMAGE DATA OF A BODY PART AND THERMAL IMAGER," which claims priority to and the benefit of Great Britain Patent Application Number 1811620.2 filed on 16 Jul. 2018, where both of these applications are incorporated herein by reference in their entirety.

FIELD OF THE INVENTION

The present invention relates to a system and method for obtaining thermal image data of a body part and to a thermal imager that is particularly applicable for use in identifying diabetic foot ulceration.

BACKGROUND TO THE INVENTION

People with diabetes are prone to serious ulcers in their feet, which can become infected and ultimately require amputation. Early detection is critical to improve patient outcomes, enabling doctors to intervene to protect the foot before skin breakdown occurs and, in cases of infection, to give antibiotics promptly.

It is estimated that up to 50% of diabetics experience foot neuropathy which can result in undetected extensive skin damage, leading to ulceration (diabetic foot ulceration (DFU)), infection and amputation. This train of events is largely avoidable with an estimated 80% reduction in amputations if early preventative action is taken. Mortality rates after DFU and amputation are high, with up to 70% of people dying within 5 years of having an amputation and around 50% dying within 5 years of developing a diabetic foot ulcer. Besides the adverse effect on patients, it has been estimated that DFU and contingent complications cost the National Health Service in England and Wales in excess of £1 billion per year.

Medical studies have identified that there is a persistent increase in skin temperature of >2° C. for up to 10 days before skin breakdown takes place. Typically, before there are any visible signs of infection or abnormality in the feet, the skin temperature rises. This is not necessarily infection-related and can also be caused by tissue breaking down from friction and the subsequent increased blood flow to the area.

Achieving measurements of the necessary accuracy and being able to monitor the temperatures of the foot over time is a particular challenge.

Most physicians routinely examine a diabetic patient's feet visually, test for touch sensitivity, and palpate them to detect local temperature variations possibly indicating an incipient lesion (pre-ulceration). These manual techniques are notoriously inaccurate and can, where there is concern over ulceration, be supplemented by thermal mapping (in which the foot contacts a measurement device or platform for temperature measurement) or thermal imaging diagnostic techniques. However, commercial off the shelf thermal mapping and thermal imaging devices and techniques also have various shortcomings.

Firstly, there are no known devices that have size, cost and ease of use suitable for use outside of a large medical practice or laboratory. Ideally, such devices should be available for use by podiatrists, care homes and the like without needing highly skilled operators.

Secondly, even with highly skilled operators, existing devices are not able to provide temperatures with clinically relevant uncertainties (i.e. better than ±0.3° C. (k=2). For example, a number of DFU current thermal mapping devices require actual contact of the patient's feet with the device. In such a case (contact-based measurement) the device's temperature and thermophysical properties will perturb the object's (foot) temperature and will therefore impact accuracy of measurements.

Even when other areas of potential variance and error have been minimised or eliminated, it has been determined that accuracy of commercial off the shelf thermal imagers used for absolute temperature measurement varies considerably. In one study ("Performance tests of thermal imaging systems to assess their suitability for quantitative temperature Measurements" by Whittam et al, 12th International Conference on Quantitative Infrared Thermography, France, Bordeaux, 7-11 Jul. 2014, https://www.ndt.net/search/docs.php3?showForm=off&id=17768), it was identified that five out of six thermal imaging devices tested demonstrated errors in temperature measurement that fell outside of the manufacturer's own stated error margin at a distance of 1 m from the measurement target. Given that the manufacturer's stated error margin was typically ±2° C. and the thermal imaging devices could not repeatedly and uniformly achieve this error margin, they are not capable of providing clinically relevant temperatures (uncertainties<±0.3° C.) and it is highly questionable whether they could be relied upon to give an early warning of a persistent increase in skin temperature of >2° C.

Reliable foot temperature comparisons over time require accurate spatial registration of the foot each time an image is obtained. This can be challenging because operators (and their abilities and approaches employed) may differ and foot position and size may change between patients and between measurements, distorting the foot temperature measurement accuracy.

There therefore appears substantial room for improvement of devices and approaches. If the temperature increase associated with neuropathy could be accurately identified in a timely manner it is expected that it should be straightforward to greatly reduce ulceration through (for example) preventative off-loading.

STATEMENT OF INVENTION

According to an aspect of the present invention, there is provided a computer-implemented method for obtaining thermal image data of a body part comprising:

receiving image data of a body part, the image data including thermal image data, the thermal image data including thermal image data of the body part and background thermal image data;

applying a classifier to the image data to detect a profile of the body part, the classifier being configured to use image data other than the thermal image data to perform the detection;

generating a mask from said profile;

applying the mask to the thermal image data to remove the background thermal image data and obtain thermal image data of the body part.

Embodiments of the present invention concern a method and system in which additional data is used to guide extraction of thermal images of body parts. The additional data may be other image data (such as visual image or a stereo visual image) of the same scene. The additional data may also (or alternatively) include training data that has been used to train a machine learning or artificial intelligence system such as a neural network, genetic algorithm or the like. For example, a training bank of images of feet (visual, thermal images, other image types or some combination) can be used to train the classifier to determine a profile from presented image data and that profile can then be used to generate a mask and extract the thermal image data of the body part. In preferred embodiments, the system is used in a hand-held thermal imaging system for identifying potential or predicted foot ulceration from captured thermal imagery.

In thermal imagers, there is a general assumption that the foreground imaged object will be much hotter than the surrounding environment (background) so that background subtraction can be applied. However, this assumption does not always hold true. Background temperatures cannot be guaranteed to differ substantially from the foreground body part and may vary depending on time of day, season or environment (for example it is not uncommon in hospitals and care homes where embodiments of the invention may be used to have relatively high background temperatures to provide comfort to those who have limited movement or are bed ridden). Additionally, DFU's are common around the big toe and ball of the foot. Where such areas are cooler (due to circulation issues, for example), there is a risk that areas of the foot may not be properly differentiated from the background. Embodiments of the present invention seek to address this by utilising additional image data to more clearly differentiate edges of the body parts.

It will be appreciated that approaches may be operated in parallel or in conjunction, for example a neural network producing what it considers to be the profile from the thermal image data and this being contrasted with the profile generated from a machine vision system from stereo image of the scene. Alternatively, the neural network could operate on the stereo image and the resultant profile then applied to the thermal image.

The image data may include visual image data captured from the same scene as the thermal image data, the classifier being configured to detect the profile of the body part from the visual image data.

The image data may include visual stereo image data captured from the same scene as the thermal image data.

The classifier may comprise an artificial neural network or other artificial intelligence system trained from image data of body parts to detect the profile of the body part.

The classifier may be configured to determine a spatial orientation of the body part, the method further including the step of modifying spatial orientation of the obtained thermal image data of the body part in dependence on the determined spatial orientation to match a default spatial orientation.

Although much of the current focus is on thermal imaging for detecting onset of foot neuropathy and triggering advanced preventative measures, the approaches set out in this application are also applicable to other body parts such as eyes, limbs and other body parts of human and/or animal subjects.

The inventors of the present application have been conceived a non-contact thermal imaging device, system and method that addresses many of the shortcomings of known thermal imaging diagnostic devices and systems.

BRIEF DESCRIPTION OF THE DRAWINGS

Embodiments of the present invention will now be described by way of example only with reference to the accompanying drawings in which.

DETAILED DESCRIPTION

Figure 1:
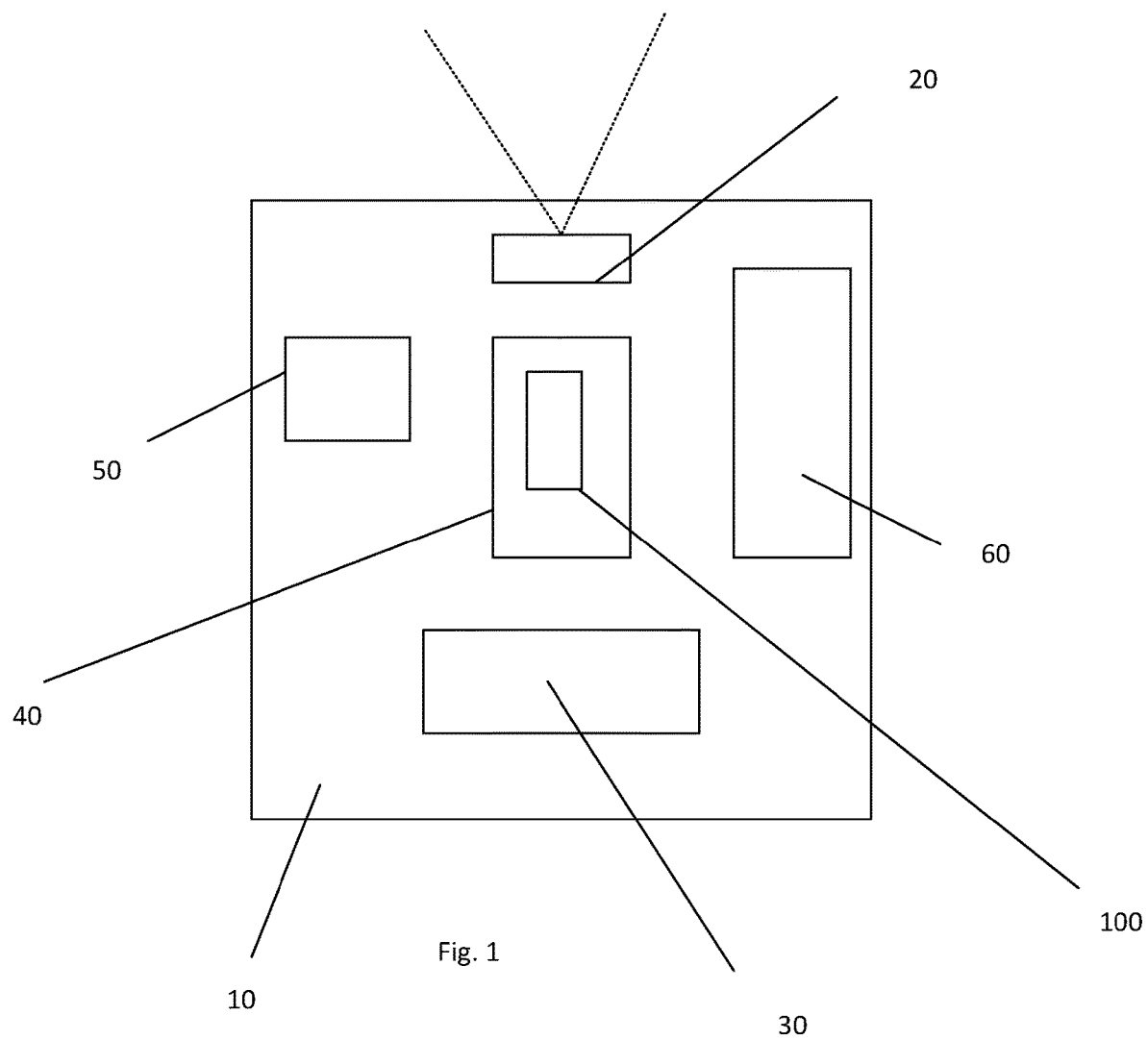
FIG. 1 is a schematic diagram of a thermal imager according to an embodiment of the present invention.

FIG. 1 is a schematic diagram of a thermal imager according to an embodiment of the present invention.

The thermal imager 10 is preferably of a hand-held form factor and includes a thermal camera 20, a battery power source 30, a processor 40, a data repository 50 and a touchscreen display 60.

The thermal imager also includes a thermal image processing system 100 that is executed by the processor 40 to obtain thermal image data on a body part from raw thermal image data captured by the thermal camera 20. Further details on the thermal image processing system are set out below with reference to FIGS. 2-4.

In operation, the user positions the thermal imager such that the body part to be imaged is within the field of view of the thermal camera. Output of the thermal camera may be displayed on-screen to aid this.

Preferably, the thermal imager provides the user with a live scene display and the imager is orientated by the user such that the object of interest (foot) is in image. Alignment tools are preferably used such as a distance pointer/on screen overlays (akin to visual camera systems) etc. When the user is happy with orientation a button is depressed (or screen tap) and an image is captured.

Optionally, alignment guides may be projected from the device using LED's or the like. In such an arrangement, the user points the alignment guides at specific features of the target area(s) of the body part or alternatively positions the body part/thermal imager such that the body part falls inside the projected alignment guides.

A thermal image of the body part is then produced by the thermal image processing system 100 and written to the data repository 50. This may be displayed on screen, compared to prior thermal images of the body part in the data repository 50, to an image of the opposite foot and/or used to trigger an alert and/or highlight areas of potential concern exhibiting temperatures indicative of inflammation.

Where inflammation may arise in different parts/sides of a body part, the thermal imager 10 may include capture protocols in the form of computer program instructions that are executed by the processor 40 and guide the user (for example by on-screen prompts on the display 60) to follow a predetermined measurement protocol to capture predetermined views of the body part. In the case of a foot, these view may include (in no particular order): left foot (sole—plantar), right foot (sole—plantar), left foot (top—dorsal), right foot (top—dorsal), left foot (outer side—lateral), right foot (outer side—lateral), left foot (inner side—medial), right foot (inner side—medial).

Preferably, the thermal imager is a micro-bolometer array operating at 8-14 μm. The micro-bolometer array is preferably a staring focal plane array in which its pixel elements are micro-bolometers that are sensitive to infrared radiation/temperature. In one embodiment, the pixels are each 17-25 μm in size. Infrared radiation is emitted by every object above absolute 0. Infrared radiation has a strong ($T^4$) relationship with temperature—such that temperature of an object can be determined from measuring its emitted infrared radiation. A thermal image is captured by measuring the infrared radiation received at each pixel of the array. This data may be encoded/compressed for storage efficiency (such as run length encoding) and can be handled using image processing in a similar way to a pixel-based visual image.

It will be appreciated that the touchscreen display could be replaced by another user interface such as a display and keypad or it could be replaced by some other arrangement such as a Bluetooth connection to a smartphone or the like (which then acts as a remote user interface for controlling the thermal imaging system 10 and viewing imagery).

The thermal imager 10 may also include an I/O system for wired or wireless communication of obtained thermal images or other data. The battery power source 30 may be rechargeable and/or replaceable.

Figure 2:
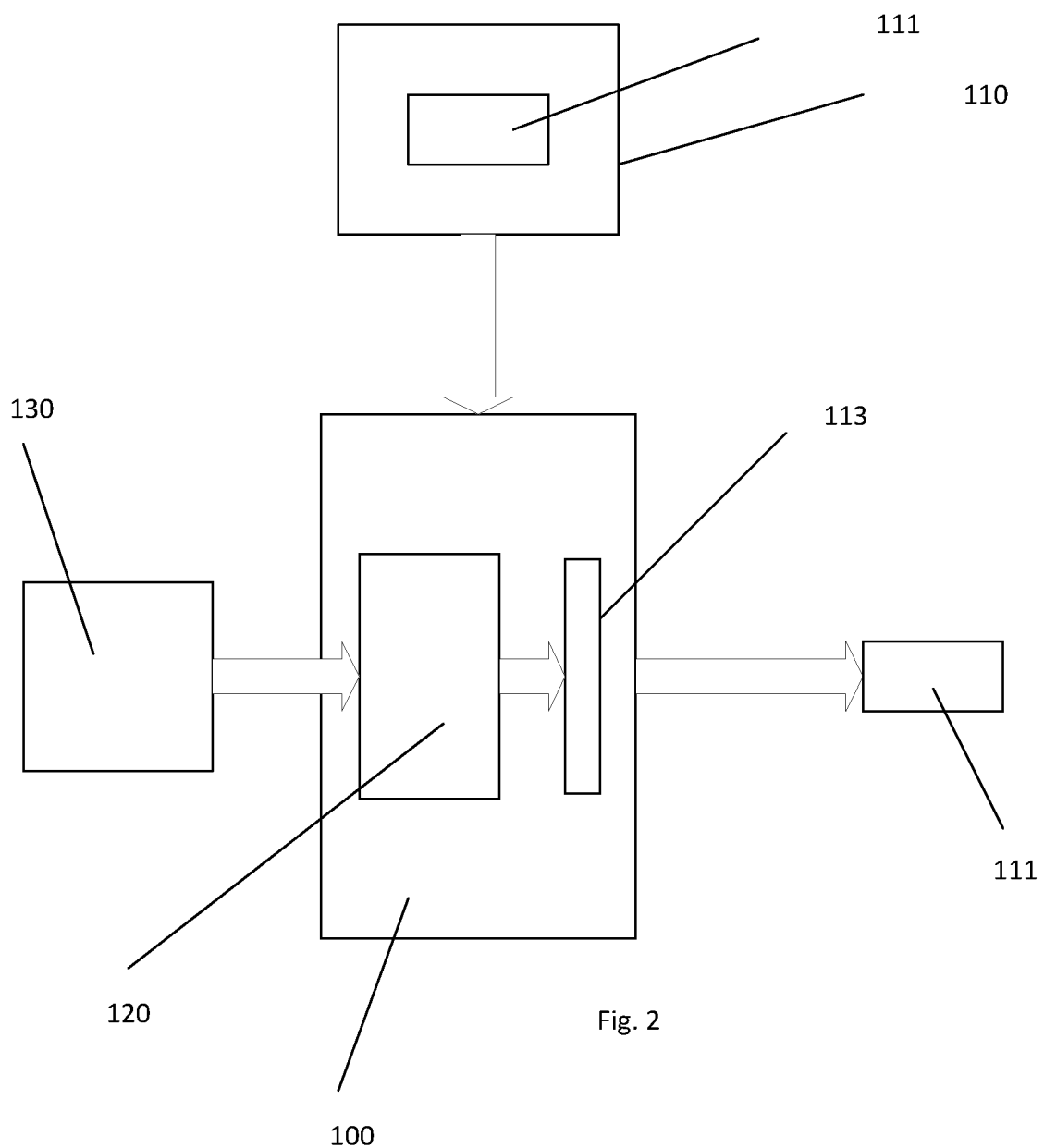
FIG. 2 is a schematic diagram of a thermal image processing system according to an embodiment of the present invention.

FIG. 2 is a schematic diagram of a thermal image processing system for obtaining thermal image data of a body part according to an embodiment of the present invention.

The thermal image processing system 100 is configured to receive thermal image data 110. The thermal image data includes both thermal image data of the body part 111 and background thermal image data 112.

In order to extract the thermal image data of the body part 111, the thermal image processing system 100 applies a classifier 120 to detect a profile of the body part. The classifier uses image data 130 other than the thermal image data 110 to perform the detection, examples of which are described with reference to FIGS. 3 and 4 below.

Once a profile has been detected, it is used by the thermal image processing system to generate a mask 113. The thermal image processing system then applies the mask 113 to the thermal image data 110 to remove the background thermal image data 112 and obtain thermal image data of the body part 111.

Figure 3:
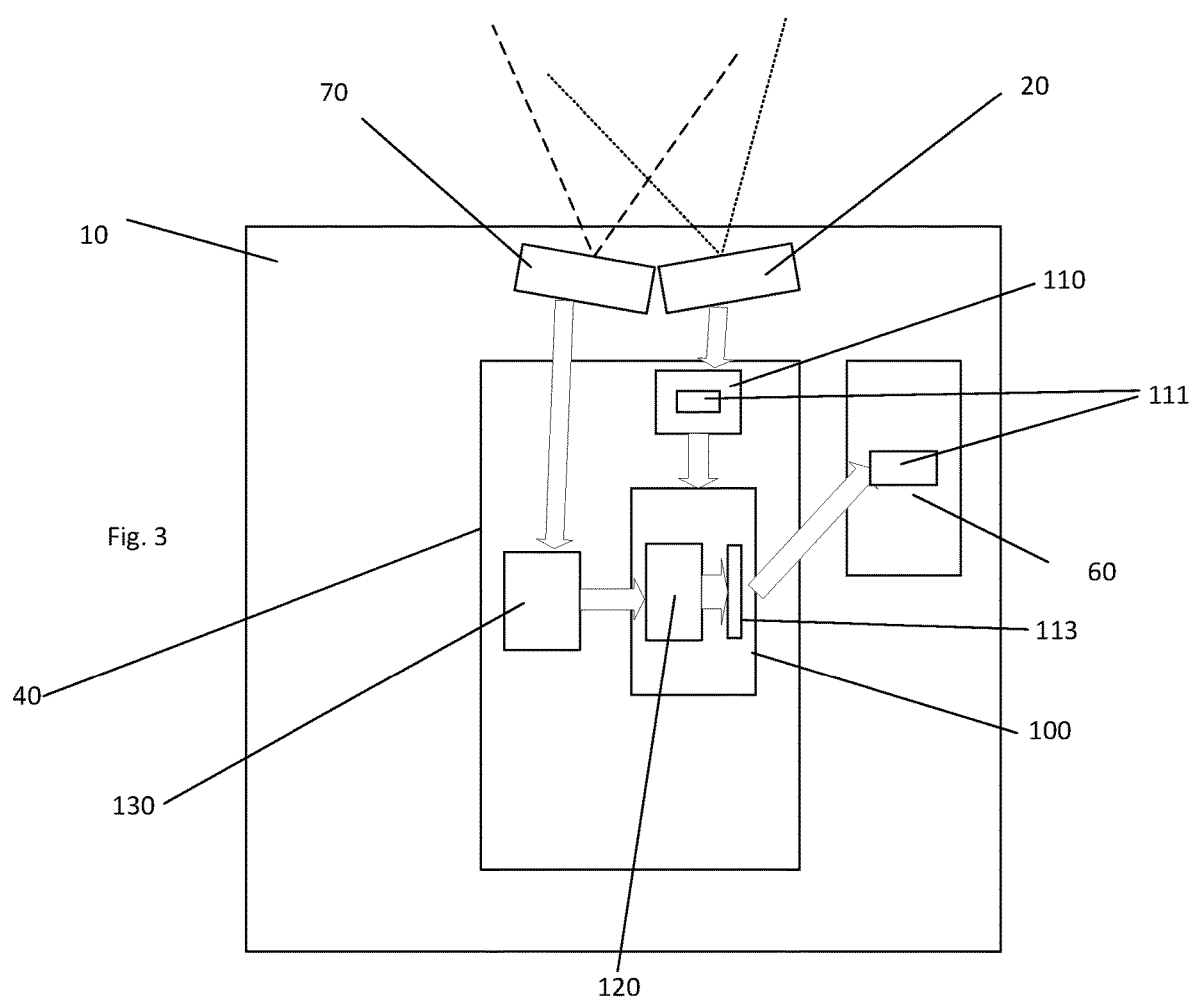
FIG. 3 is a schematic diagram illustrating aspects of the system of FIG. 2 in more detail.

FIG. 3 is a schematic diagram illustrating aspects of the system of FIG. 2 in more detail.

In one embodiment, the thermal imager may also include a visual imaging sensor 70 that is configured to capture the visual spectrum of the imaged scene to generate visual image data 130a (this may be stored separately to the thermal image data 110 or they may be stored collectively). The visual imaging sensor 70 may capture an RGB image of the scene, for example.

Figure 4:
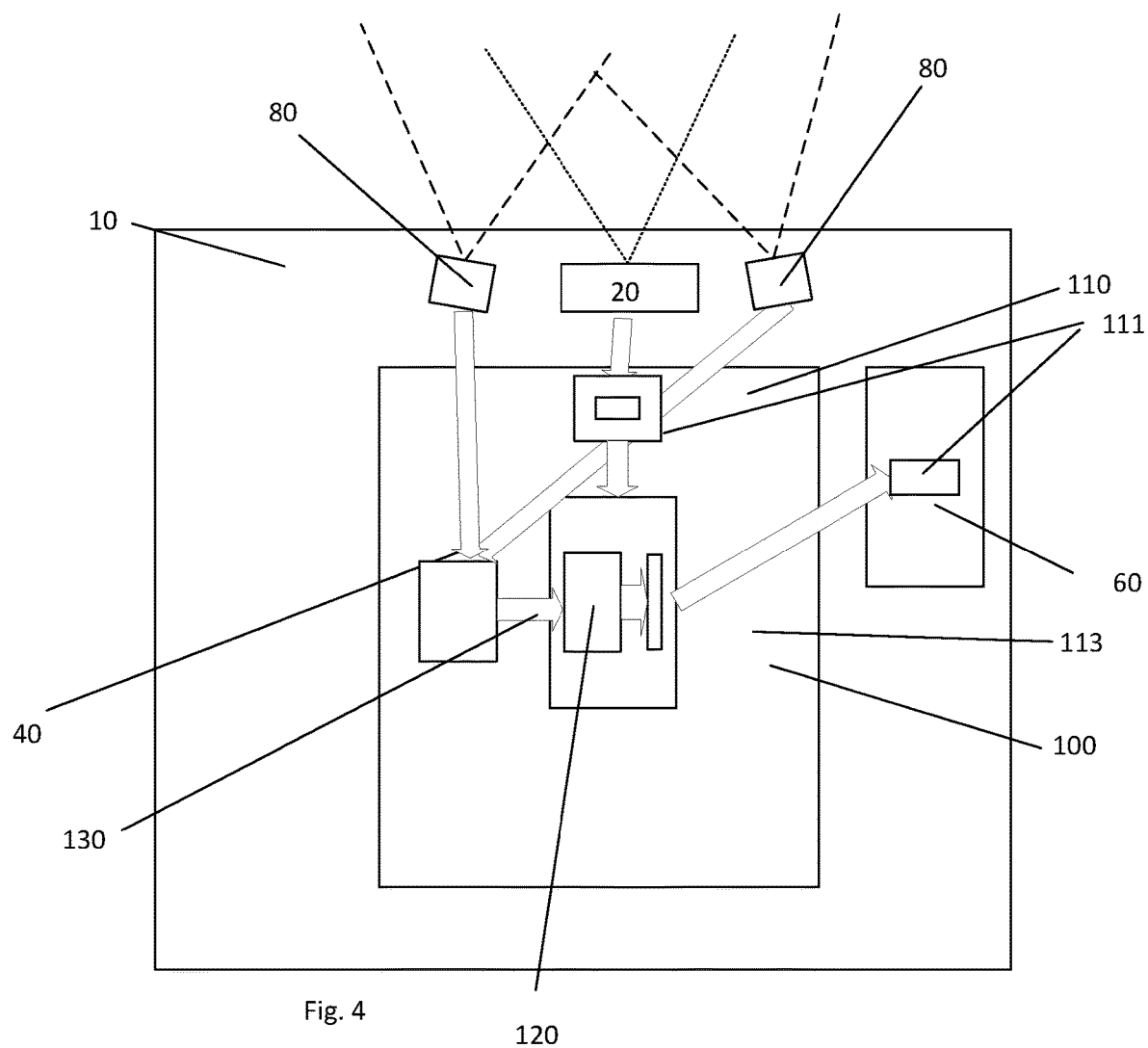
FIG. 4 is a schematic diagram illustrating aspects of the system of FIG. 2 in more detail; and, FIG. 5 is a schematic diagram illustrating alternate aspects of the system of FIG. 2 in more detail.

FIG. 4 is a schematic diagram illustrating aspects of the system of FIG. 2 in more detail.

In a preferred embodiment, the thermal imager includes a stereo visual imaging sensor 80 (in one embodiment this is a pair of visual imaging sensors having a predetermined orientation and distance therebetween such that stereo image processing can be performed).

The stereo visual imaging sensor 80 is configured to capture a stereo image of the visual spectrum of the imaged scene to generate visual image data 130b (as before, this may be stored separately to the thermal image data 110 or they may be stored collectively). The visual imaging sensor 80 may capture a pair of RGB images of the scene, for example. In this embodiment, the classifier 120 uses the stereo visual image data 130b to detect the profile of the body part from the visual image data.

The classifier may optionally be configured to determine a spatial orientation of the body part from the image data 130. For example, the classifier may use the stereo visual image data to determine spatial orientation of the body part and the thermal image processing system may then modify spatial orientation of the obtained thermal image data of the body part in dependence on the determined spatial orientation to match a default spatial orientation.

In one embodiment, the thermal image processing system 100 may use the stereo visual image data 130b to generate a 3D model (preferably a 3D topography mesh) of the body part onto which the thermal imaging data is registered. The 3D model may be generated using photometric stereo, structure from motion or other approaches.

Further data may be overlaid onto the 3D model such as interfacial pressure data, thermal measurements from the thermal image data such as Max, Min, Mean, Span, Histogram etc.

FIG. 5 is a schematic diagram illustrating alternate aspects of the system of FIG. 2 in more detail.

In this embodiment, the classifier 120 includes an artificial neural network that has been trained from image data 130 other than the thermal image data including image data of body parts and is configured to detect the profile of the body part. In this embodiment, the image data other than the thermal image data may or may not have been of that particular person's body part and may include thermal image data, visual image data or other image data (or a combination).

The neural network may, for example, be a convolutional neural network. The artificial neural network may be self-organising, feed-forward It is to be appreciated that certain embodiments of the invention as discussed above may be incorporated as code (e.g., a software algorithm or program) residing in firmware and/or on computer useable medium having control logic for enabling execution on a computer system having a computer processor. Such a computer system typically includes memory storage configured to provide output from execution of the code which configures a processor in accordance with the execution. The code can be arranged as firmware or software, and can be organized as a set of modules such as discrete code modules, function calls, procedure calls or objects in an object-oriented programming environment. If implemented using modules, the code can comprise a single module or a plurality of modules that operate in cooperation with one another.

Optional embodiments of the invention can be understood as including the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth.

Although illustrated embodiments of the present invention have been described, it should be understood that various changes, substitutions, and alterations can be made by one of ordinary skill in the art without departing from the present invention which is defined by the recitations in the claims below and equivalents thereof.

The invention claimed is:

1. A computer-implemented method for obtaining thermal image data of a body part, the method being executed in a handheld device including a display and a thermal imager and comprising:
   receiving image data of a body part, the image data including thermal image data, the thermal image data including thermal image data of the body part and background thermal image data;
   applying a classifier to the image data to detect a profile of the body part, the classifier being configured to use image data other than the thermal image data to perform the detection;
   generating a mask from said profile;
   applying the mask to the thermal image data to remove the background thermal image data and obtain thermal image data of the body part, wherein the image data includes visual image data captured from the same scene as the thermal image data, the classifier detecting the profile of the body part from the visual image data, wherein the image data includes visual stereo image data captured from the same scene as the thermal image data,
   the method further comprising displaying via the display a live scene display of the scene to be captured by the thermal camera to guide positioning of the handheld device by the user such that the body part is in image.

2. The method of claim 1, wherein the step of applying a classifier includes applying an artificial neural network trained from image data of body parts to the received image data to detect the profile of the body part.

3. The method of claim 1, further comprising determining a spatial orientation of the body part by the classifier from the visual stereo image data and modifying spatial orientation of the obtained thermal image data of the body part in dependence on the determined spatial orientation to match a default spatial orientation.

4. A handheld thermal imager including a thermal camera, a display, and a processor,
   the processor being configured to execute computer program code for executing a classifier, including:
   computer program code configured to receive image data of a body part, the image data including thermal image data from the thermal camera, the thermal image data including thermal image data of the body part and background thermal image data;
   computer program code configured to apply a classifier to the image data to detect a profile of the body part, the classifier being configured to use image data other than the thermal image data to perform the detection;
   computer program code configured to generate a mask from said profile;
   computer program code to apply the mask to the thermal image data to remove the background thermal image data and obtain thermal image data of the body part, further comprising a visual imager configured to capture visual image data on the same scene as the thermal image data, the computer program code configured to apply the classifier detecting the profile of the body part from the visual image data, wherein the visual imager includes a stereo visual imager, the display configured to display a live scene display of the scene to be captured by the thermal camera.

5. The thermal imager of claim 4, wherein the computer program code configured to apply a classifier includes computer program code configured to apply an artificial neural network trained from image data of body parts to the received image data to detect the profile of the body part.

6. The thermal imager of claim 4, wherein the processor is further configured to execute computer program code to determine a spatial orientation of the body part by the classifier from stereo image data from the stereo visual imager and modify spatial orientation of the obtained thermal image data of the body part in dependence on the determined spatial orientation to match a default spatial orientation.

7. A computer-implemented method for obtaining thermal image data of a body part comprising:
   receiving image data of a body part, the image data including thermal image data, the thermal image data including thermal image data of the body part and background thermal image data;
   applying a classifier to the image data to detect a profile of the body part, the classifier being configured to use image data other than the thermal image data to perform the detection;
   generating a mask from said profile;
   applying the mask to the thermal image data to remove the background thermal image data and obtain thermal image data of the body part, wherein the image data includes visual image data captured from the same scene as the thermal image data, the classifier detecting the profile of the body part from the visual image data, wherein the image data includes visual stereo image data captured from the same scene as the thermal image data, the method further comprising generating a 3D model of the body part and projecting the thermal imaging data into the 3D model.

8. The thermal imager of claim 4, further comprising a visual alignment tool to guide alignment of the body part.

9. The thermal imager of claim 8, wherein the visual alignment tool comprises an on-screen overlay on the display to guide alignment of the body part.

10. The thermal imager of claim 8, wherein the visual alignment tool comprises a light emitter configured to project visual alignment guides from the handheld device to be positioned at or around the body part.

11. A handheld thermal imager including a thermal camera, a visual imager configured to capture visual image data on the same scene as imaged by the thermal camera wherein the visual imager includes a stereo visual imager, and a processor,
   the processor being configured to execute computer program code for executing a classifier, including:
   computer program code configured to receive image data of a body part, the image data including thermal image data from the thermal camera, the thermal image data including thermal image data of the body part and background thermal image data;
   computer program code configured to apply a classifier to the image data to detect a profile of the body part, the classifier being configured to use image data other than the thermal image data to perform the detection;
   computer program code configured to generate a mask from said profile;
   computer program code to apply the mask to the thermal image data to remove the background thermal image data and obtain thermal image data of the body part, the computer program code configured to apply the classifier detecting the profile of the body part from the visual image data, the processor being further configured to execute computer program code to generate a 3D model of the body part and project the thermal imaging data into the 3D model.

12. The method of claim 7, wherein the step of applying a classifier includes applying an artificial neural network trained from image data of body parts to the received image data to detect the profile of the body part.

13. The method of claim 7, further comprising determining a spatial orientation of the body part by the classifier from the visual stereo image data and modifying spatial orientation of the obtained thermal image data of the body part in dependence on the determined spatial orientation to match a default spatial orientation.

* * * * *